United States Patent
Enomoto et al.

(10) Patent No.: US 10,208,302 B2
(45) Date of Patent: *Feb. 19, 2019

(54) COMPOSITE MATERIAL AND METHOD OF MANUFACTURING COMPOSITE MATERIAL

(71) Applicant: Koito Manufacturing Co., Ltd., Tokyo (JP)

(72) Inventors: Kiminori Enomoto, Shizuoka (JP); Hisayoshi Daicho, Shizuoka (JP); Yu Shinomiya, Shizuoka (JP)

(73) Assignee: KOITO MANUFACTURING CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/977,324

(22) Filed: Dec. 21, 2015

(65) Prior Publication Data

US 2016/0102302 A1    Apr. 14, 2016

Related U.S. Application Data

(63) Continuation of application No. PCT/JP2014/003203, filed on Jun. 16, 2014.

(30) Foreign Application Priority Data

Jul. 3, 2013    (JP) ................................ 2013-140067

(51) Int. Cl.
| | | |
|---|---|---|
| *C12N 11/14* | (2006.01) | |
| *C01B 25/32* | (2006.01) | |
| *C01B 25/455* | (2006.01) | |
| *C30B 29/14* | (2006.01) | |
| *A61L 27/42* | (2006.01) | |
| *A61L 27/46* | (2006.01) | |
| *C30B 7/10* | (2006.01) | |
| *B01J 27/185* | (2006.01) | |
| *B01J 35/00* | (2006.01) | |
| *C30B 29/60* | (2006.01) | |
| *B01J 27/18* | (2006.01) | |

(52) U.S. Cl.
CPC ............ *C12N 11/14* (2013.01); *A61L 27/425* (2013.01); *A61L 27/46* (2013.01); *B01J 27/1856* (2013.01); *B01J 35/002* (2013.01); *B01J 35/004* (2013.01); *C01B 25/32* (2013.01); *C01B 25/455* (2013.01); *C30B 7/105* (2013.01); *C30B 29/14* (2013.01); *C30B 29/602* (2013.01); *C30B 29/607* (2013.01); *A61L 2430/02* (2013.01); *B01J 27/1806* (2013.01); *C01P 2004/13* (2013.01)

(58) Field of Classification Search
CPC ................. C01B 25/32; C01B 25/321; A61F 2310/00293; C30B 29/14; C30B 29/607; C30B 15/00; C30B 29/602; C30B 9/06; A61L 27/12; A61L 27/425; C01P 2004/13
See application file for complete search history.

(56) References Cited

U.S. PATENT DOCUMENTS

2003/0219624 A1    11/2003    Aso et al.

FOREIGN PATENT DOCUMENTS

| CN | 104220649 A | 12/2014 |
|---|---|---|
| EP | 2837715 A1 | 2/2015 |
| EP | 2898944 A1 | 7/2015 |
| JP | 01238869 A | 9/1989 |
| JP | 03-080098 A | 4/1991 |
| JP | 07-196314 A | 8/1995 |
| JP | H09-095787 A | 4/1997 |
| JP | H09-138234 | 5/1997 |
| JP | 09-169794 A | 6/1997 |
| JP | 11-180705 A | 7/1999 |
| JP | 2000-095577 A | 4/2000 |
| JP | 2000-271488 A | 10/2000 |
| JP | 2011-011971 A | 1/2011 |
| WO | 2013-153749 A1 | 10/2013 |
| WO | 2014-045534 A1 | 3/2014 |

OTHER PUBLICATIONS

Ma et al. Solvothermal preparation of hydroxyapatite microtubes in water/N,N-dimethylformamide mixed solvents. Materials Letters. 2008;62:1642-1645.*

Hung et al. Titanium surface modified by hydroxyapatite coating for dental implants. Surface & Coatings Technology. 2013;231:337-345.*

Czajka-Jakubowska et al. The effect of the surface characteristics of various substrates on fluorapatite crystal growth, alignment, and spatial orientation. Med Sci Monit. 2009;15(6):MT84-88.*

Katsuya Teshima et al., "Direct Growth of Highly Crystalline, Idiomorphic Fluorapatite Crystals on a Polymer Substrate," Crystal Growth & Design, Aug. 4, 2009 (Web), pp. 3832-3834, vol. 9, No. 9, American Chemical Society.

Ming-Guo Ma et al., "Solvothermal preparation of hydroxyapatite microtubes in water/N,N-dimethylformamide mixed solvents," Materials Letters 62 (2008), Sep. 29, 2007 (Web), pp. 1642-1645, Elsevier B.V.

Yan Zhou et al., "Single-crystal microtubes of a novel apatite-type compound, (Na2.5Bi2.5)(PO4)3(F,OH), with well-faceted hexagonal cross sections," The Royal Society of Chemistry, May 27, 2009 (Web), pp. 1863-1867, CrystEngComm.

Junfeng Hui et al, "Monodisperse F-Substituted Hydroxyapatite Single-Crystal Nanotubes with Amphiphilic Surface Properties," Inorganic Chemistry Communication, May 28, 2009 (Web), pp. 5614-5616, American Chemical Society.

International Search Report from International Application No. PCT/JP2014/003203, dated Sep. 16, 2014.

(Continued)

Primary Examiner — Lynn Y Fan

(57) ABSTRACT

A composite material includes: an apatite crystal in the form of a tube; and a functional component accommodated in the apatite crystal tube and constituted by a material having physical properties different from those of the apatite crystal. The apatite crystal may be a monocrystal given by the general formula $M^2{}_5(PO_4)_3X$, where $M^2$ denotes at least one element selected from the group consisting of divalent alkali earth metals and Eu, and X denotes at least one element or molecule selected from the group consisting of halogens and OH.

9 Claims, 3 Drawing Sheets

(56) References Cited

OTHER PUBLICATIONS

International Preliminary Report on Patentability from International Application No. PCT/P2014/003203, dated Jan. 5, 2016.
P.R.C. Patent Office action on patentability in counterpart Chinese App. No. 201480037344.8, dated Sep. 26, 2016.
Partial Supplementary European Search Report from European Pat. App. No. 14820599.0, dated Mar. 2, 2017.
Vijay Mohan Bhatnagar, "The Melting Points of Synthetic Apatites," Mineralogical Magazine, Dec. 1, 1969, pp. 527-528, vol. 37, No. 288, Mineralogical Society, Twickenham, U.K.
European Search Report from European Pat. App. No. 14820599.0, dated Apr. 6, 2017.
De-Li Jiang, "Study on the Preparation of Phosphonio-Nanocomposites and the Catalytic Performance Thereof," doctoral dissertation, China Dissertation Database, Aug. 24, 2011, pp. 37-42, Jiangsu Univ., China.
State Intellectual Property Office of the P.R.C. action on patentability in counterpart Chinese App. No. 201480037344.8, dated Jun. 9, 2017.
Office Action for corresponding CN application No. 201480037344.8, (Dec. 27, 2017), SIPO.
Office Action for corresponding EP application EP14820599.0, dated Nov. 23, 2017 (Nov. 23, 2017), EPO.
Office Action dated May 29, 2018 issued for corresponding Japanese Patent Application No. 2015-525029.

* cited by examiner

COMPOSITE MATERIAL AND METHOD OF MANUFACTURING COMPOSITE MATERIAL

CROSS-REFERENCE TO RELATED APPLICATIONS

This application is based upon and claims the benefit of priority from the prior Japanese Patent Application No. 2013-140067, filed on Jul. 3, 2013 and International Patent Application No. PCT/JP2014/003203, filed on Jun. 16, 2014, the entire content of each of which is incorporated herein by reference.

BACKGROUND OF THE INVENTION

1. Field of the Invention

The present invention relates to crystalline apatites finding application in broad-ranging fields as functional materials.

2. Description of the Related Art

Advances in the development of apatite-based materials as phosphors and biofunctional materials have been made in recent years. A known example of apatite-based crystals of this sort is apatite monocrystals in the form of solid hexagonal prisms (Non-Patent Document 1). Also, a method of using needlelike hydroxyapatite whiskers to isolate proteins has been proposed (reference is made to Patent Document 1).

Patent Document 1 JP9-169794

Non-Patent Document 1 Katsuya Teshima et al., "Direct growth of highly crystalline, idiomorphic fluorapatite crystals on a polymer substrate," *Crystal Growth & Design*, 2009, Vol. 9, No. 9, pp. 3832-3834

In finding application in a variety of uses, apatite-based materials have room for improvement in terms of their form and constituents suited to those uses.

SUMMARY OF THE INVENTION

The present invention addresses this situation and a purpose thereof is to afford a novel composite material having tubular apatite crystals.

To address the aforementioned issue, a composite material according to an embodiment of the present invention comprises: an apatite crystal in the form of a tube; and a functional component accommodated in the apatite crystal tube and constituted by a material of physical properties different from those of the apatite crystal.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

Figure 1:
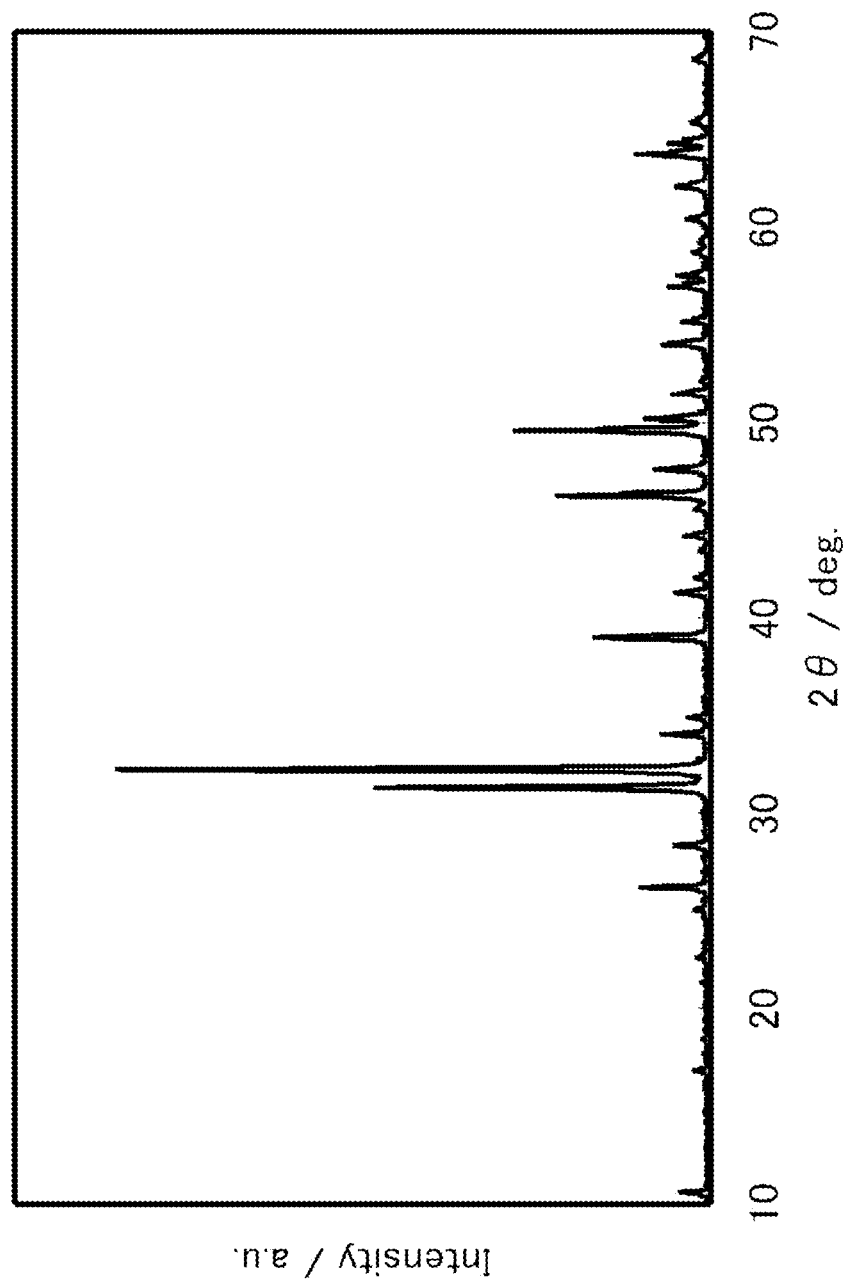
FIG. 1 is an exemplary X-ray analysis pattern of a crystal formed by the method in Examples.

A composite material according to an embodiment of the present invention comprises: an apatite crystal in the form of a tube; and a functional component accommodated in the apatite crystal tube and constituted by a material of physical properties different from those of the apatite crystal.

This embodiment yields novel functionality that cannot be obtained from tubular apatite crystal alone.

The apatite crystal may be a monocrystal given by the general formula $M^2{}_5(PO_4)_3X$, where $M^2$ denotes at least one element selected from the group consisting of divalent alkali earth metals and Eu, and X denotes at least one element or molecule selected from the group consisting of halogen elements and OH. In this way, a tubular apatite monocrystal can be easily obtained.

The transmittance of the apatite crystal to visible light may be 65% or higher.

The functional component may be constituted by a material of higher rigidity than that of the apatite crystal. This realizes strength that is difficult to obtain from apatite crystal alone.

The functional part may be constituted by a photocatalytic substance. Placing the photocatalytic substance inside the tubular apatite crystal realizes a photocatalytic material of improved performance. The functional part may be constituted by an enzyme. This allows the composite material to be used as, for example, a bioreactor.

The apatite crystal may be a hexagonal prism in outer form, and a hole-opening formed in either of top or bottom surfaces of the hexagonal prism may be of hexagonal form.

The apatite crystal may have a tube-hole inner diameter of 3 nm-800 μm.

The apatite crystal may be 1 μm-1 mm in diameter.

The apatite crystal may measure 2 μm-4 mm lengthwise.

Another embodiment of the present invention relates to a method of manufacturing a composite material. The method comprises: placing, tube-internally in an apatite crystal in the form of a tube, a metallic material of rigidity higher than that of the apatite crystal; and fusing and immobilizing the metallic material with a laser beam transmitted through the apatite crystal.

According to this embodiment, the metallic material can be easily immobilized inside the apatite crystal tube. The metallic material may be a single kind of metal or an alloy. Still alternatively, the metallic material may contain a substance other than metal. The fusing point of the metal material may be lower than that of the apatite crystal.

Still another embodiment of the present invention relates to a method of manufacturing a composite material. The method comprises: adsorbing avidin molecules tube-internally into an apatite crystal in the form of a tube; and infusing the tube interior with a solution containing a biotin-labeled enzyme to immobilize the enzyme inside the tube.

In this way, an enzyme can be easily immobilized in the apatite crystal tube.

Optional combinations of the aforementioned constituting elements, and implementations of the invention in the form of methods, apparatuses, and systems may also be practiced as additional modes of the present invention.

A description will be given of suitable embodiments of the present invention with reference to the drawings. Like numerals are used to represent like elements, members, and processes and a description will be omitted as appropriate. The embodiments of the present invention are not limited to those described and appropriate combinations or replacements of the features of the embodiment are also encompassed by the present invention.

The apatite crystal according to an embodiment is a tubular apatite monocrystal. The apatite crystal is given by a general formula $M^2{}_5(PO_4)_3X$ ($M^2$ denotes at least one element selected from the group consisting of a divalent alkali earth metal and Eu, and X denotes at least one element or molecule selected from the group consisting of a halogen element and OH). In this way, a tubular apatite monocrystal can be easily obtained. For example, the alkali earth metal may be Ca, Sr, Ba, Ra, Mg, or Be. The halogen element may be, for example, F, Cl, Br, or I.

A description will be given of a method of manufacturing a tubular apatite monocrystal by way of examples. Embodiments will be described in specific details by way of examples. Examples 1-7 are directed to a method of synthesizing a chlorapatite monocrystal. Examples 8-10 are directed to a method of synthesizing a hydroxyapatite monocrystal. Synthesizing methods include the flux method, coprecipitation method, sol-gel method, etc.

Chlorapatite Monocrystal

Example 1: Flux Method

First, $CaHPO_4$, $CaCO_3$, and $CaCl_2$ are metered and mixed uniformly at a molar ratio Ca:P:Cl=5:3:1. Thereafter, NaCl is added so that the chlorapatite concentration is 0.15 mol %. The mixture is heated to 800-1100° C. in a platinum crucible at a temperature increase rate 100-500° C./h. Synthesis is allowed to proceed for 48 hours at a synthesis temperature of 800-1100° C. and then the temperature is lowered from 800-1100° C. to 500° C. at a temperature decrease rate 5-300° C./h. Thereafter, the synthesized product is cooled naturally to a normal temperature. After calcination, the product is cleaned carefully using pure hot water (about 80° C.) to extract a chlorapatite monocrystal.

Example 2: Flux Method

First, $CaHPO_4$, $CaCO_3$, and $CaCl_2$ are metered and mixed uniformly at a molar ratio Ca:P:Cl=5:3:1. Thereafter, a large amount of $CaCl_2$ is added. The mixture is heated to 800-1100° C. in a platinum crucible at a temperature increase rate 100-500° C./h. Synthesis is allowed to proceed for 48 hours at a synthesis temperature of 800-1100° C. and then the temperature is lowered from 800-1100° C. to 500° C. at a temperature decrease rate 5-300° C./h. Thereafter, the synthesized product is cooled naturally to a normal temperature. After calcination, the product is cleaned carefully using pure hot water (about 80° C.) to extract a chlorapatite monocrystal.

Example 3: Flux Method

First, $CaHPO_4$, $CaCO_3$, $SrCo_3$, $CaCl_2$, and $SrCl_2$ are metered and mixed uniformly at a molar ratio Ca+Sr:P:Cl=5:3:1. Thereafter, $SrCl_2$ is added so that the chlorapatite concentration is 0.15 mol %. The mixture is heated to 800-1100° C. in a platinum crucible at a temperature increase rate 100-500° C./h. Synthesis is allowed to proceed for 48 hours at a synthesis temperature of 800-1100° C. and then the temperature is lowered from 800-1100° C. to 500° C. at a temperature decrease rate 5-300° C./h. Thereafter, the synthesized product is cooled naturally to a normal temperature. After calcination, the product is cleaned carefully using pure hot water (about 80° C.) to extract a chlorapatite monocrystal.

Example 4: Flux Method

First, $CaHPO_4$, $CaCO_3$, $MgCo_3$, $CaCl_2$, and $MgCl_2$ are metered and mixed uniformly at a molar ratio Ca+Mg:P:Cl=5:3:1. Thereafter, $MgCl_2$ is added so that the chlorapatite concentration is 0.15 mol %. The mixture is heated to 800-1100° C. in a platinum crucible at a temperature increase rate 100-500° C./h. Synthesis is allowed to proceed for 48 hours at a synthesis temperature of 800-1100° C. and then the temperature is lowered from 800-1100° C. to 500° C. at a temperature decrease rate 5-300° C./h. Thereafter, the synthesized product is cooled naturally to a normal temperature. After calcination, the product is cleaned carefully using pure hot water (about 80° C.) to extract a chlorapatite monocrystal.

Example 5: Coprecipitation Method

First, calcium nitrate and calcium chloride are dissolved in pure water. Phosphoric acid is dropped in the solution. A precipitate (seed crystal) is produced by adjusting pH to 5-9. The seed crystal prepared by the coprecipitation method is allowed to grow by the Czochralski method. A $CaCl_2$—$Ca_2ClPO_4$ system with a $Ca_2ClPO_4$ concentration of 15 mol % is heated to 1200°. The seed crystal is immersed in the resultant high-temperature solution. By pulling up the crystal while cooling the solution gradually from 1200° C. to 1050° C., a chlorapatite monocrystal is obtained.

Example 6: Sol-Gel Method

First, calcium nitrate is dissolved in distilled water. Ethoxide phosphate is added (total molar concentration of calcium and phosphorus=0.05 mol/L) and the mixture is churned. Concentrated hydrochloric acid (1 mol of chlorine for 1 mol of calcium) is then added to the mixture. The solution is dried for 2 hours at 60° C. The distilled water is then removed so as to obtain a seed crystal. The seed crystal prepared by the sol-gel method is allowed to grow by the Czochralski method. A $CaCl_2$—$Ca_2ClPO_4$ system with a $Ca_2ClPO_4$ concentration of 15 mol % is heated to 1200°. The seed crystal is immersed in the resultant high-temperature solution. By pulling up the crystal while cooling the solution gradually from 1200° C. to 1050° C., a chlorapatite monocrystal is obtained.

Example 7: Sol-Gel Method

First, calcium ethoxide is dissolved in distilled water. Phosphoric acid is added (total molar concentration of calcium and phosphorus=0.05 mol/L) and the mixture is churned. Concentrated hydrochloric acid is then added to the mixture. The solution is dried for 2 hours at 60° C. Distilled water is removed so as to obtain a seed crystal. The seed crystal prepared by the sol-gel method is allowed to grow by the Czochralski method. A $CaCl_2$—$Ca_2ClPO_4$ system with a $Ca_2ClPO_4$ concentration of 15 mol % is heated to 1200°. The seed crystal is immersed in the resultant high-temperature solution. By pulling up the crystal while cooling the solution gradually from 1200° C. to 1050° C., a chlorapatite monocrystal is obtained.

Hydroxyapatite Monocrystal

Example 8: Coprecipitation Method

A 0.5 mol/L aqueous solution of phosphoric acid is dropped in a 0.3 mol/L suspended calcium hydrate liquid. A monocrystal precipitate (seed crystal) is obtained by adjusting pH to 5-9 to promote formation of a monocrystal. The seed crystal prepared by the coprecipitation method is allowed to grow by the Czochralski method. Calcium hydrate is heated to 1650° C. The seed crystal is immersed in the resultant high-temperature solution. By pulling up the crystal while cooling the solution gradually from 1650° C. to 1000° C., a needle-shaped hydroxyapatite monocrystal is obtained.

Example 9: Hydrothermal Synthesis Method

First, 63.37 g of lactic acid is dissolved in 1 liter of water. 22.11 g of calcium hydrate is then added. Further, 6.92 g of phosphoric acid is dissolved into the mixture. An autoclave is filled with the slurry prepared in this way. The slurry is subject to a hydrothermal process for 5 hours at 165° C. The slurry thus processed is filtered and dried so as to obtain a hydroxyapatite monocrystal.

Example 10: Sol-Gel Method $1.0 \times 10^{-2}$ mol of calcium diethoxide is dissolved in 6.5 ml of ethylene glycol. $6.0 \times 10^{-3}$ mol of triethyl phosphite is taken and dissolved for use in a predetermined amount of ethanol such that the composition ratio in hydroxyapatite is Ca/P=5/3. Thereafter, a mixed solution comprising the ethylene glycol solution of calcium diethoxide and triethyl phosphite solution is churned for 2 hours so as to produce a precipitate. The solution is heated for 2 hours at 200° C. so as to obtain a seed crystal. The seed crystal prepared by the sol-gel method is allowed to grow by the Czochralski method. Calcium hydrate is heated to 1650° C. The seed crystal is immersed in the resultant high-temperature solution. By pulling up the crystal while cooling the solution gradually from 1650° C. to 1000° C., a needle-shaped hydroxyapatite monocrystal is obtained.

Transformation from Chlorapatite into Hydroxyapatite

Example 11

The chlorapatite monocrystal (20 mg) is introduced in a platinum capsule (2.6 mmφ, length=3.3 mm) along with a 6.25 (mol/L) aqueous solution (40 μl) of potassium hydroxide (KOH), and the capsule is sealed by fusing a sealing material. The hydrothermal process is performed in an autoclave of test tube type by using water as a pressure medium under the condition of 100 MPa. The temperature increase rate is 20° C. per minute. The processing temperature is constantly 400° C. and the processing time is 48 hours. In this way, a hydroxyapatite monocrystal is obtained.

Example 12

The chlorapatite monocrystal (20 mg) is heated 1300° C. Water vapor is introduced in the kiln to induce a reaction over a period of 2 weeks, thereby transforming the chlorapatite monocrystal into a hydroxyapatite monocrystal.

Composition

The composition of the chlorapatite monocrystal formed by the methods in Examples was studied. FIG. 1 is an exemplary X-ray analysis pattern of the crystal formed by the methods in Examples. As shown in FIG. 1, the crystal comprises a single layer of chlorapatite monocrystal $Ca_5(PO_4)_3Cl$.

Component

The chlorapatite tube monocrystal was then subject to element analysis. The analysis of the crystal showed that Ca=39.10 mass %, P=18.00 mass %, and CL=5.30 mass %.

Shape

Figure 2:
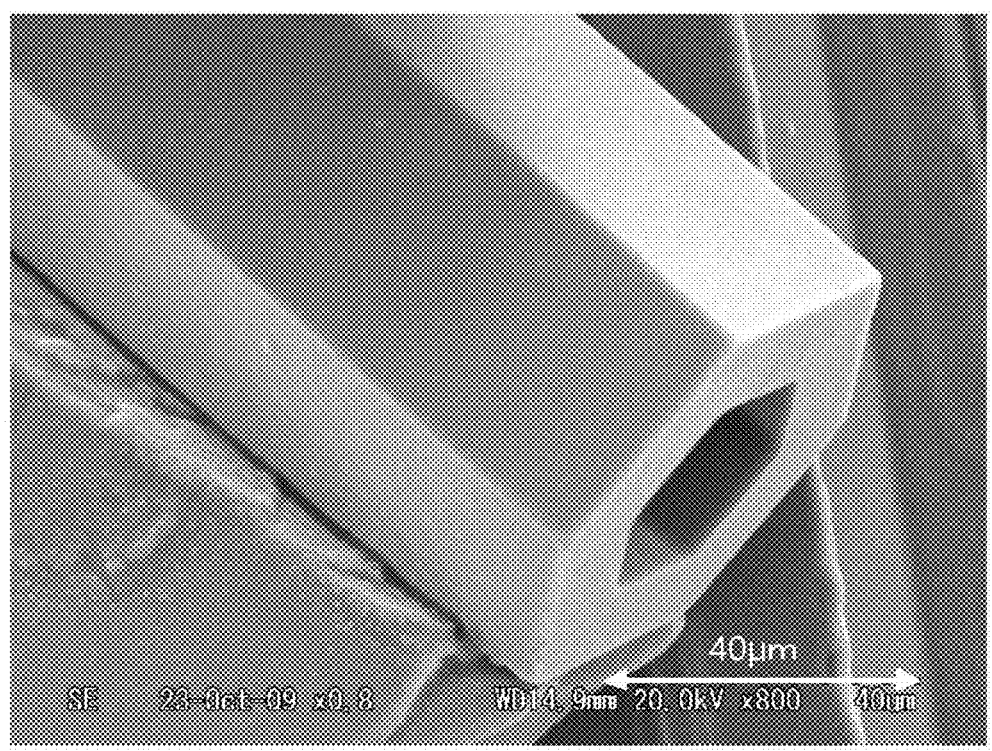
FIG. 2 is a photograph of an exemplary chlorapatite tube monocrystal observed by an SEM.

The shape of the chlorapatite tube monocrystal was then observed by a scanning electron microscope (SEM). FIG. 2 is a photograph of an exemplary chlorapatite tube monocrystal observed by the SEM. As shown in FIG. 2, the apatite monocrystal according to the embodiment is tubular and the outer form of the crystal is a hexagonal prism. Further, the aperture of the hole formed on the top surface or bottom surface of the hexagonal prism is hexagonal in shape. For this reason, the thickness of the tube outer wall is substantially uniform.

SEM observation showed that the tubular monocrystals are in various sizes and forms. For example, the inner diameter of the hole of the opening of the tubular monocrystal is about 3 nm-800 μm, and, preferably, about 10 nm-60 μm. The diameter of the tubular monocrystal is about 20 nm-1 μm. The length of the tubular monocrystal in the longitudinal direction is about 50 nm-4 mm. The transmittance of the tubular monocrystal to visible light is 65% or higher.

Applications

Our study has shown that a composite material including the aforementioned apatite crystal in the form of a tube, and a functional component accommodated in the apatite crystal tube and formed by a material having physical properties different from those of the apatite crystal provides a novel function that cannot be provided by tubular apatite crystal alone. Applications of the novel composite material having tubular apatite will be described in specific detail below.

First Embodiment

In this embodiment, an application of the aforementioned hexagonal tubular apatite monocrystal to a reinforcing material for an artificial bone will be described. More specifically, we devised a composite material in which a tubular monocrystal of apatite as a biomaterial is used, as a reinforcing member for improving the strength of an artificial bone. Unlike the related-art solid needle-shaped apatite crystal, a tubular apatite crystal can receive a strong metal such as titanium inserted into the tube. Therefore, higher strength than the related-art reinforcing member can be obtained.

Aspects of the performance required of a reinforcing member for use in an artificial bone are ( ) high biocompatibility and (ii) high strength. A high aspect ratio needle-shaped apatite as a biomaterial, when used as a reinforcing member, has low strength and so is insufficient as a reinforcing member for an artificial bone used in a movable region. A reinforcing member having high biocompatibility and having a higher strength than the related-art biomaterial apatite has been called for.

We have come to hold an idea of a composite material for a highly biocompatible and strong reinforcing member, produced by inserting a strong metal material such as titanium, magnesium, and aluminum into the aforementioned apatite monocrystal that is characteristically tubular and mainly composed of calcium phosphate. For example, the diameter of the apatite monocrystal of a hollow (tubular) hexagonal prism shape in an application like this is about 1 μm-1 mm. Further, the inner diameter of the hole of the opening of the tubular monocrystal is, for example, about 0.5 μm-800 μm. Still further, the length of the tubular monocrystal in the longitudinal direction is, for example, about 2 μm-4 mm.

It is desirable to make sure that the core of the reinforcing member be strong in order to improve the strength of the reinforcing member itself. For this purpose, it is useful to insert a metal material such as aluminum into the tubular apatite monocrystal.

Method of Manufacturing a Reinforcing Member

A tubular hydroxyapatite monocrystal having a length of 200 μm, a diameter of 40 μm, and an inner diameter of 20 μm of the hole of the opening was obtained according to the method described in Example 1 or Example 12. The apatite monocrystal is a substance that transmits visible light. An aluminum wire was inserted into the hollow portion of the tubular hydroxyapatite monocrystal thus obtained. The aluminum wire was immobilized inside the tube by heating wire locally from outside for 1 hour at about 700° C., using a YAG laser, thereby producing a reinforcing member. It is preferable that the visible light transmittance of the tubular apatite monocrystal be 65% or higher. Since the tubular apatite monocrystal is transparent, laser light is transmitted through the crystal to heat the aluminum wire selectively. Accordingly, the damage exerted by the heat of the laser on the apatite monocrystal is reduced.

In this way, the method of manufacturing a composite material (reinforcing member) according to the embodiment places, tube-internally in tubular apatite crystal, a metal material (titanium, aluminum, magnesium, an alloy thereof, etc.) more rigid than the apatite crystal, and fuses and immobilizes the metal material by laser light transmitted through the apatite crystal. In this way, the metal material can be easily immobilized in the apatite crystal tube. The metal material may be a single kind of metal (titanium, aluminum, magnesium, etc.) or an alloy thereof. Still alternatively, the metal material may contain a substance other than metal. The fusing point of the metal material may be lower than that of the apatite crystal. In this case, the metal material may be fused selectively without fusing the apatite monocrystal.

A tubular apatite monocrystal is used in the composite material describes above. In the composite material according to a comparative example, a needle-shaped apatite monocrystal is used. More specifically, a 0.5 mol/L aqueous solution of phosphoric acid was dropped in a 0.3 mol/L suspended calcium hydrate liquid. A monocrystal precipitate was obtained by adjusting pH to 5-9 to promote formation of a monocrystal. A needle-shaped hydroxyapatite monocrystal having a length of 200 μm and an outer diameter of 40 μm was obtained by allowing the precipitate to grow at 1200° C. for 48 hours.

Method of Manufacturing an Artificial Bone Material

A pulsed current sintering device was used to sinter CaO as an air cell control material at 700° C. for 10 minutes. The CaO sintered compact was coarsely ground and classified to isolate powders of about 100-200 μm. The spherical hydroxyapatite powders having an average particle diameter of 10 μm and the classified air cell control material were mixed uniformly. The blend ratio of the air cell control material is 50 vol %. Stoichiometrically, the Ca/P ratio in hydroxyapatite is 1.67.

10 vol % of the reinforcing member according to the inventive example (tubular) or the comparative example (needle-shaped) was added to the powder mix of hydroxyapatite/air cell control material. The mixture was used to fill a carbon dice having a diameter of 15 mm and sintered in vacuum at 1000° C. for 10 minutes, using a pulsed current sintering device. The temperature increase rate during sintering was about 100° C./min and the mixture was naturally cooled in the device. The temperature of the dice was measured. It was learned from powder X-ray analysis that the sintered compact is comprised of hydroxyapatite and CaO. No reaction between the compounds was observed.

Evaluation of Performance for Improving Strength

The break strength, breaking energy, and fracture toughness value of a sample produced by adding 10 vol % of the reinforcing material according to inventive example and the comparative example to an artificial bone material were measured. The result is shown in Table 1.

| | Break strength [MPa] | Breaking energy [Arbitrary unit] | Fracture toughness [MPa*m$^{1/2}$] |
| --- | --- | --- | --- |
| Example | 1200 | 2.5 | 10.8 |
| Comparative example | 700 | 0.6 | 5.0 |

The break strength [MPa] in Table 1 represents a breaking stress (load per unit area) in a phenomenon where a solid-state material is broken into two or more parts under an external force. The break strength represents a measurement of J toughness value determined by measuring the three-point strength in accordance with Japanese Industrial Standard (JIS).

Fracture toughness (KIC) [MPa*m$^{1/2}$] is a stress intensity factor required for a crack to develop. A test piece of the same size as the test piece for break strength measurement was used. A diamond cutter was used to form a U groove having a width of 0.1 mm and a depth of 0.75 mm at the center of the test piece. Measurements were made at room temperature at a span of 30 mm and at a cross head speed of 0.75 mm/min, and KIC was determined according to the following equation.

$$KIC = Y \sigma a^{1/2}$$

where Y: form factor, σ: bending strength, a: crack length.

Breaking energy is defined as a total energy exerted on the material before breakage. A material with a large breaking energy is referred to as "rigid". Breaking energy was calculated from the area formed by the stress-distortion curve obtained in a fracture toughness test and the cross sectional area of fractured surface of the test piece.

As shown in Table 1, the break strength, breaking energy, and fracture toughness value of an artificial bone reinforced by the composite material (inventive example) produced by filling a tubular apatite monocrystal by a metal material are all higher than those of an artificial bone in which a needle-shaped apatite monocrystal (comparative example) is added. Thus, the strength that can hardly be obtained with an apatite crystal alone is realized by forming the functional part by a material more rigid than the apatite crystal. It should be known that the composite material according to the first embodiment is suitable as a reinforcing member.

Second Embodiment

In this embodiment, an application of the aforementioned hexagonal tubular apatite monocrystal to a photocatalyst will be described. Hydroxyapatite coated with titanium oxide or the like does not contain metal atoms that are harmful to the environment. The hydroxyapatite carrier itself has the capability to adsorb organic substance or the like, and the titanium oxide coating absorbs light ranging from visible light to ultraviolet light. Therefore, excellent photocatalytic activity is exhibited.

The apatite coated with a photocatalytic substance in itself is often in powder form for ease of use, etc. If this is used to fill a column, the column is easily clogged so that liquid permeability cannot be secured. Another problem is that the interior of the column cannot be sufficiently irradiated with light. One approach to prevent clogging is to use hydroxyapatite having a large particle diameter. Disadvantageously, however, an increase in particle diameter results in a smaller specific surface area and lower photocatalytic performance.

The composite material according to the embodiment can realize excellent photocatalytic applications because the tube-shape of the apatite crystal enlarges the surface area and the formation of a titanium oxide coating on the transparent apatite monocrystal surface activates the photocatalytic reaction induced by the light transmitted through the apatite monocrystal. A description will be given below of a method of manufacturing a composite material according to the embodiment having a photocatalytic function with reference to Example 13 and Example 14.

Example 13

A tubular hydroxyapatite monocrystal having a composition $Ca_5(PO_4)_3(OH)$, and having a length of 0.3-2 mm and an inner diameter of 80-300 nm of the hole of the opening was obtained according to the method described in Examples 1-12 above. The monocrystal was immersed in a room-temperature glass coating agent containing 0.1-5 wt % of Ti-modified apatite for 1 hour, cleaned in pure water, and dried at 80° C. for 12 hours. The monocrystal was annealed for 1 hour at 700° C. A portion of the apatite tube surface is replaced by titanium so as to impart the crystal with photocatalytic function.

Example 14

A tubular chlorapatite monocrystal having a composition $Ca_5(PO_4)_3Cl$, and having a length of 0.3-2 mm and an inner diameter of 50-200 nm of the hole of the opening was obtained according to the method described in Examples 1-12 above. The monocrystal was immersed in a room-temperature glass coating agent containing 0.1-5 wt % of Ti-modified apatite for 1 hour, cleaned in pure water, and dried at 80° C. for 12 hours. The monocrystal was annealed for 1 hour at 700° C. A portion of the apatite tube surface is replaced by titanium so as to impart the crystal with photocatalytic function.

Measurement of Photocatalytic Activity: Acetaldehyde Gas Decomposition

The photocatalytic activity was evaluated, using the composite material obtained according to Example 13 and Example 14 and having photocatalytic function. First, sample powders of composite materials according to the respective Examples were weighed so as to have a surface area based on specific surface area measurements. The sample thus weighed is used to fill the bottom of a glass container topped by a quartz glass in uniform thickness. The interior of the container is replaced by synthetic air (20 volume % of oxygen, 80 volume % of nitrogen).

Subsequently, acetaldehyde is injected into the container so that the acetaldehyde gas concentration is 1 volume %. The mixture is left at rest in a dark place until the acetaldehyde gas reaches adsorption equilibrium with the sample powders. Thereafter, the mixture is started to be irradiated with light from a light source of a xenon lamp (3 hours after the mixture is left at rest in a dark place). The gas is extracted by a cylinder 1 hour after the adsorption equilibrium is reached (2 hours after the mixture is left at rest in a dark place), 2 hours later (3 hours after the mixture is left at rest in a dark place), and 3 hours later (4 hours after the mixture is left at rest in a dark place). The $CO_2$ gas concentration was measured by using gas chromatography. 2 hours after the mixture was irradiate by light from the light source, a $CO_2$ gas concentration of 5 g/L (liter) or higher was observed and high photocatalytic activity was exhibited in every sample.

Thus, a composite material comprised of a tubular apatite crystal as a carrier and a photocatalytic substance as a functional part accommodated in the tube allows the interior of a column closely filled with the composite material to be irradiated with light. By placing the photocatalytic substance on the inner wall instead of using it to fill the entirety of the tube, gas or liquid can pass through the tube. This increases chances of contact between a substance sought to be decomposed and the photocatalytic substance and provides high photocatalytic activity. More specifically, the tubular apatite crystal has 1.5-4 times the specific surface area [$cm^2/g$] as compared to the needle-shaped apatite crystal so that the photocatalytic performance is 1.5-4 times higher. Since the photocatalytic substance can be placed inside the tubular apatite crystal, the composite material according to the embodiment can exhibit improved photocatalytic performance.

Third Embodiment

In this embodiment, an application of the aforementioned hexagonal tubular apatite monocrystal to a bioreactor will be described. Unlike inorganic catalysts such as platinum that are widely used in industry, enzymes are biocatalysts and functions primarily in vivo. Specificity and selectivity of enzymes are utilized to adsorb or decompose organic substances such as sugar or protein. Enzyme reaction proceeds relatively quickly in an aqueous solution at normal temperature and normal pressure and contributes to chemical industry and instrumental analysis by simplifying reaction routes to synthesize organic substances. Due to its low impact on environment, enzyme reaction could help realize low-carbon society.

However, enzymes used in liquid are basically disposed after use and increase the cost accordingly. One approach to utilize valuable enzymes fruitfully is to create a bioreactor built to immobilize an enzyme in an insoluble carrier, allow the carrier to contact an organic source material, and cause the enzyme to work and function as a catalyst.

According to this embodiment, a tubular apatite monocrystal useful as a biomaterial is used as a carrier to immobilize an enzyme. The adsorption action of apatite is exploited to immobilize the enzyme to form a bioreactor column. Thus, the functional part according to this embodiment is formed by an immobilized enzyme.

Two major approaches are available to immobilize an enzyme (e.g., protein or amino acid) in the aforementioned tubular apatite monocrystal.

(1) A cation adsorption site ($Ca^{2+}$, etc.) or an anion adsorption site ($HPO_4^{2-}$, $PO_4^{3-}$, $OH^-$, $X^-$, etc.; X is a halogen element) is induced on an apatite, depending on its pH. In this approach, the enzyme is immobilized in the adsorption site by electrostatic adsorption. Whether to adsorb the enzyme in the cation adsorption site or the anion adsorption site may be selected as appropriate depending on the type of enzyme.

(2) A bioreactor column is prepared by electrostatically adsorbing molecules of avidin, a basic glycoprotein known to have bioaffinity with enzymes, to the apatite and by immobilizing an enzyme labeled by biotin, a hydrosoluble vitamin, to the avidin molecules by bioaffinity binding. Because biotin can be attached to enzyme molecules without causing the enzyme to lose its activity, an enzyme labeled by biotin is obtained. By binding the enzyme labeled by biotin to the avidin molecules adsorbed to the apatite, the enzyme can be immobilized in the apatite tube. The enzyme immobilized may be selected from various types including glycolytic enzyme, proteolytic enzyme, etc.

A description will now be given of an exemplary method of labeling an enzyme by biotin. First, an enzyme and a biotin labeling agent are suspended in a buffered solution (pH8.5) so that the molar ratio of the mixture is 1:2-1:10. The mixture, infused with the suspended liquid, is then incubated in a constant temperature bath (25° C.) for 2-4 hours. The resultant solution is analyzed by chromatography so as to isolate the labeled enzyme.

A description will be given below of a method, according to the embodiment, of manufacturing a composite material having an enzyme, with reference to Examples 15 through 17.

Example 15

A tubular hydroxyapatite monocrystal having a composition $Ca_5(PO_4)_3(OH)$, and having a length of 0.3-2 mm and an inner diameter of 80-600 nm of the hole of the opening was obtained according to the method described in Examples 1-12 above. The apatite tube is then infused with a solution produced by suspending amylase in a buffered solution of pH5-6.5. The composite is incubated in a hot bath of 20-35° C. for 8 hours so as to immobilize the amylase in the apatite tube.

Example 16

A tubular chlorapatite monocrystal having a composition $Ca_5(PO_4)_3Cl$, and having a length of 0.3-2 mm and an inner diameter of 3-40 nm of the hole of the opening was obtained according to the method described in Examples 1-12 above. The apatite tube is then infused with a solution produced by suspending glucoamylase in a buffered solution of pH7-9. The composite is incubated in a hot bath of 20-35° C. for 8 hours so as to immobilize the glucoamylase in the apatite tube.

Example 17

A tubular chlorapatite monocrystal having a composition $Ca_5(PO_4)_3Cl$, and having a length of 0.5-4 mm and an inner diameter of 3-40 nm of the hole of the opening was obtained according to the method described in Examples 1-12 above. The apatite tube is then infused with a solution produced by dispersing avidin molecules in a buffered solution of pH6-8. The composite is incubated in a hot bath of 20-35° C. for 4 hours so as to immobilize the avidin molecules in the apatite tube electrostatically. An enzyme labeled by biotin is then suspended in a buffered solution of pH6-8 and the suspended solution is used to infuse the apatite tube at 20-25° C. for 30 minutes, thereby immobilizing the enzyme in the apatite tube by a biotin-avidin reaction. In the case of this method, enzymes such as amylase, cellulase, xylase, racemase, etc. that differ in molar weight and isoelectric point can be easily immobilized.

Figure 3:
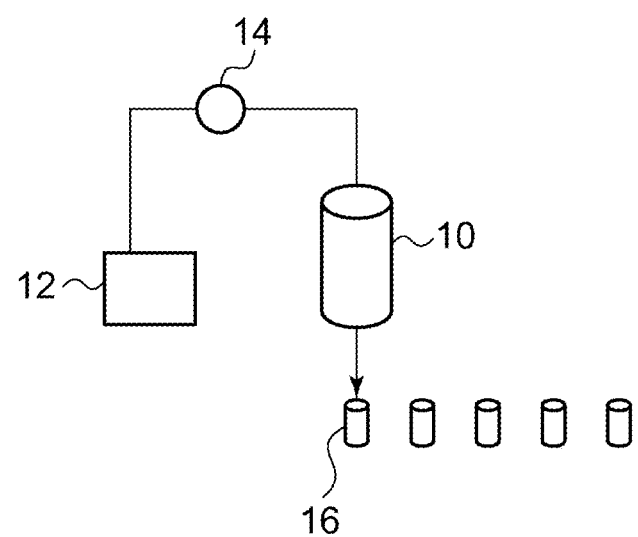
FIG. 3 schematically shows a device in which the bioreactor column according to an embodiment is used.

A description will now be given of the benefit of a tubular apatite monocrystal in which an enzyme is immobilized. FIG. 3 schematically shows a device in which the bioreactor column according to this embodiment is used. First, a column having an inner diameter of 10 mm and a length of 100 mm was filled with a tubular apatite monocrystal in which glucoamylase is immobilized according to the biotin-avidin method, so as to prepare a bioreactor column 10. A buffered solution containing oligosaccharide and adjusted to pH7-8 was supplied from a source material container 12 to the bioreactor column 10 by using a tube pump 14. The buffered solution was supplied in a continuous steady-state operation at a liquid temperature of 30° C. and a liquid measure of 0.3 ml/minute.

The solution discharged from the bioreactor column 10 was collected in a sample container 16 at 1 hour intervals. The content of the sample was isolated and identified by thin-layer chromatography. It was revealed that most of the oligosaccharide is decomposed into glucose in the sample solution at all points of time that the sample was collected and that the bioreactor column 10 was functioning sufficiently.

Described above is an explanation based on an exemplary embodiment. The embodiment is intended to be illustrative only and it will be obvious to those skilled in the art that various modifications to constituting elements and processes could be developed and that such modifications are also within the scope of the present invention.

INDUSTRIAL APPLICABILITY

The apatite crystal according to the embodiment can be used as a variety of functional materials including fluorescent bodies.

The invention claimed is:
1. A composite material comprising:
   a tubular apatite monocrystal given by the general formula $M^2{}_5(PO_4)_3X$,
   where $M^2$ denotes at least one element selected from the group consisting of divalent alkali earth metals and Eu, and X denotes Cl; and
   a functional component accommodated in the tubular apatite monocrystal and constituted by a material of physical properties different from those of the tubular apatite monocrystal.
2. The composite material according to claim 1, wherein the tubular apatite monocrystal has a transmittance of at least 65% with respect to visible light.
3. The composite material according to claim 1, wherein the functional component is constituted by a material of higher rigidity than that of the tubular apatite monocrystal.
4. The composite material according to claim 1, wherein the functional component is constituted by a photocatalytic substance.
5. The composite material according to claim 1, wherein the functional component is constituted by an enzyme.
6. The composite material according to claim 1, wherein an outer form of the tubular apatite monocrystal is a hexagonal prism, and an aperture of a hole formed on a top surface or bottom surface of the hexagonal prism is hexagonal in shape.
7. The composite material accordingly to claim 1, wherein the tubular apatite monocrystal has an inner diameter of 3 nm to 800 μm.
8. The composite material according to claim 1, wherein the tubular apatite monocrystal has an outer diameter of 1 μm to 1 mm.

9. The composite material according to claim 1, wherein the tubular apatite monocrystal measures 2 μm to 4 mm lengthwise.

* * * * *